United States Patent [19]

Chalifoux

[11] Patent Number: 5,342,200
[45] Date of Patent: * Aug. 30, 1994

[54] DENTAL POST AND BUR CONSTRUCTION

[76] Inventor: Paul R. Chalifoux, 6 Wellesley Ave., Wellesley, Mass. 02181

[*] Notice: The portion of the term of this patent subsequent to Jan. 11, 2011 has been disclaimed.

[21] Appl. No.: 896,388

[22] Filed: Jun. 10, 1992

Related U.S. Application Data

[63] Continuation-in-part of Ser. No. 739,670, Aug. 3, 1991, Pat. No. 5,277,583.

[51] Int. Cl.$^5$ .............................. A61C 5/08
[52] U.S. Cl. ................... 433/220; 433/221; 433/165
[58] Field of Search ............ 433/76, 165, 166, 220, 433/221

[56] References Cited

U.S. PATENT DOCUMENTS

| | | | |
|---|---|---|---|
| 635,773 | 10/1899 | Hamilton | 433/220 |
| 636,568 | 11/1899 | Seeley | 433/221 |
| 781,420 | 1/1905 | Haldeman | 433/220 |
| 791,641 | 6/1905 | McClanahan | 433/220 |
| 1,200,921 | 10/1916 | Chester | 433/165 |
| 2,807,264 | 9/1957 | Tuck | 433/166 |
| 3,508,334 | 4/1970 | Weissman | 433/76 |
| 4,820,159 | 4/1989 | Weissman | 433/165 |
| 4,990,088 | 2/1991 | Weissman | 433/165 |
| 5,094,618 | 3/1992 | Sullivan | 433/221 |

FOREIGN PATENT DOCUMENTS

| | | | |
|---|---|---|---|
| 744398 | 11/1943 | Fed. Rep. of Germany | 433/220 |
| 21126 | 2/1911 | Norway | 433/220 |

*Primary Examiner*—John J. Wilson
*Attorney, Agent, or Firm*—Paul J. Cook

[57] ABSTRACT

A dental post is provided comprising a bottom section and a stem with a slot which extends lengthwise through the stem to form a plurality of legs. The legs have wings attached thereto. The wings have cutting surfaces which are used to form indentations in a wall of a tooth bore. Kits are provided comprising the dental post and burs for forming a tooth bore to accomodate the dental post and optionally a core for supporting a tooth crown, a template for forming holes in a tooth and a key for providing support for the core.

35 Claims, 5 Drawing Sheets

DENTAL POST AND BUR CONSTRUCTION

REFERENCE TO RELATED APPLICATION

This application is a continuation-in-part of application Ser. No. 07/739,670, filed Aug. 3, 1991, now U.S. Pat. No. 5,277,583.

BACKGROUND OF THE INVENTION

This invention relates to a dental post bur construction which can be inserted into a tooth stub and can be utilized to improve retention of a dental restoration built onto the tooth stub.

It is present dental procedure to form a dental prosthetic structure onto a tooth stub for replacement of missing dentition. In this procedure, a tooth stub is initially prepared by removing the diseased or damaged top portion of a tooth to form a tooth stub. A base is formed by drilling into the root canal portion of the tooth stub to form a space into which a dental post can be inserted. Presently available dental posts include grooves on their surface designed to improve retention of the post within the tooth stub. Dental cement is employed in the bore in conjunction with the dental post to secure the post in the tooth stub. A portion of the post extends above the tooth stub upper surface so that a dental prosthesis formed in the tooth stub can be retained. Presently, the implantation of a dental post relies either upon the adherent strength of an adhesive or on lateral stress forces between the dental post and the canal wall.

Preformed posts are posts which are premade to specific dimensions with matching burs. Burs which are of matching diameter prepare the root to accept a post. A post is tried in the root and cut to the appropriate length. Cement is spun into the canal with a device called a lenticulo spiral and/or placed directly on the post. The post is placed in the canal and held in position until excess cement extrudes and the cement hardens. Most preformed posts require placing filling material around the top of the post to transfer strength from the post to the crown. This is called the core build up or post and core procedure.

There are many problems which are encountered when utilizing preformed posts. These problems include:

An inaccurate fit develops with present bur technology. Potential for perforation of the root is great with present burs.
There is inadequate resistance to rotational forces.
Root fracture caused by lateral stresses occurs.
There is weak transfer of strength from the post to the crown.

An accurately drilled hole results in good proximity of the post to the canal walls with a thin cement layer to provide greater success. The hole is inaccurate if tipping or vibrating of the bur occurs during root preparation as occurs with present drilling systems. This adds to the failure rate of preformed post systems. Drilling a straight hole for a straight post in a curved canal or drilling a hole which does not align with a canal can lead to perforation of a root and loss of a tooth. All posts must resist normal rotational forces which occur during normal or abnormal functions if there is not sufficient tooth structure to provide resistance. In general, preformed posts do not provide good stability against rotational force because they are round and rotate easily when placed in a round hole such as that provided by present bur systems. Presently, to compensate for this, a separate pin may be placed into the tooth, however, screw pins increase the likelihood of root fracture. Some systems try to make posts oval or nonsymmetrical at the top but do not supply dependable resistance and retention form. Cement merely provides suction to hold a post in position. The strength of the cement becomes a weak point to the root-post-crown relationship. Constant repeated forces of chewing causes potential breakdown in the cement. If this occurs, there is breakdown of the tooth-cement-crown interface with subsequent cement wash out and crown post failure. An uneven or excessive amount of force can cause root fracture and tooth loss. Screw type posts can exert large lateral stresses which leads to potential root fracture and tooth loss. In addition, forceful placement of cement type posts without proper venting of cement, can cause root fracture and tooth loss. Filling material is placed around a preformed post above the root to accept a crown after the post is cemented. The strength and long term stability of this material becomes a weak link in long term success of the crown. In addition, proper design of the post above the root is critical to resist rotation or dislodging of the filling material from the post.

A cast post is indicated for root canalled teeth with no clinical crown (no tooth above the height of the gums) and/or teeth with root canal spaces which are shaped in such a manner that a preformed post can not fit properly. For example, a canal may be narrow at its bottom half and diverge rapidly in the top half or it may be too oval shaped. The preformed post which is of the same diameter throughout can not accommodate these situations. When utilizing a cast post, root preparation is done by drilling to remove undercuts and obtain slight divergence from the bottom upward. The cast post technique takes an impression of a prepared root canal space. In indirect methods, an impression of the root is taken with a dental impression material. In direct methods, an acrylic pattern of the prepared root and the desired shape above the gums is achieved in the mouth. Laboratory procedures which include casting in a lost wax technique are then necessary to construct the cast post. There are many problems which are encountered when utilizing cast posts. The problems include: There is a chance of root fracture. The cast post is expensive. There is an increased possibility of root perforation. The cast post may not provide good resistance to rotational forces.

All posts need to provide venting of cement as a post is placed. A cast post is very precise fitting so it is difficult for cement to vent out of the root during placement. If cement is not allowed to vent, lateral forces can fracture the root and/or the post will not be fully seated as excess cement remains in the bottom. In addition, any bubbles or inaccuracies from the casting process can cause a poor fit and root fracture. Cast posts dramatically increases cost as compared to preformed posts because there are laboratory fees and increased chair time. For a cast post, an appointment is needed for an impression in addition to an appointment for post placement. The patient cost of a cast post is double the cost of a preformed post. The doctors laboratory cost may be five to ten times the cost to buy a preformed post.

Preparation of a root canal space must be free of any undercuts or removal of a post in its plastic or wax phase of construction will be impossible. It is often difficult to attain this as root canals tend to be complex systems of lateral canals, ribbon shapes, multiple canals, etc. Often, excessive drilling is done which removes important tooth structure and leads to a weaker root and increased chance of root fracture or perforation.

It has been proposed in U.S. Pat. Nos. 4,480,997; 4,490,116 and Re 31,948 to utilize a threaded dental post which is introduced into the bore of a tooth stub by being rotated to thread the post into position. The dental post includes a stem portion having a slot extending through the stem thickness and along its length which renders the stem being formed of two legs each having its outside surface threaded. The outside surface of the legs intimately contact the walls of the bore so that the threads on the legs can engage the walls. In addition, a spring-like connection for the two legs is provided so that a radial outward spring force is applied to the legs to force them against the bore walls. These dental posts are undesirable since a rotational force must be applied to the post to position it properly into the bore. This positioning process is undesirable since it is time consuming and causes the patient discomfort. In addition, the possibility exists that the post will be threaded too far into the tooth stub which will result in fracture of the tooth stub. Furthermore, the radially outward forces of the legs on the tooth stub can result in fracture of the tooth stub over time.

U.S. Pat. No. 1,534,409 discloses a two legged post having corrugated surfaces which fit into a root canal having generally parallel walls. This surface design materially reduces the post surface area which contacts the canal walls and thus post retention relies primarily upon cement adhesive strength.

Accordingly, it would be desirable to provide a dental post which can be inserted into the bore of a tooth stub while eliminating the need for sole reliance upon lateral stress forces with the canal wall or upon the adhesive strength of an adhesive. In addition, it would be desirable to provide a dental post which interacts with indentations in the walls of the bore by mechanical interaction in order to retain the post in the bore while minimizing or eliminating forces on the walls exerted by the post. In addition, it would be desirable to provide a system for forming a mating bore in a tooth stub for such a dental post by utilizing the dental post as the bur for forming the means for mechanical interaction between the post and the tooth stub and for properly positioning the post manually within the bore. Furthermore, it would be desirable to provide a system for utilizing such a dental post which facilitates the placement of a core and a crown.

SUMMARY OF THE INVENTION

This invention provides a dental post having a stem section formed of a plurality of spaced-apart legs, usually two or four legs, which are joined to a bottom section, possibly with vertical grooves for venting, shaped to be positioned into a bottom portion of a tooth stub bore. The legs are of a length so as to extend beyond an upper surface of the tooth stub thereby to permit manual manipulation of the legs. Each of the wings is provided with a material which permits cutting into the wall of the tooth bore by rotating or oscillating the dental post. Sets of wings with the cutting surfaces are provided, on different legs which are positioned at the same vertical height from the bottom section of the post. A dental adhesive is placed in the bore prior to placing the post within the bore. The portion of the legs extending from the tooth stub can be grasped either manually or mechanically to compress the legs together so that the wings are positioned radially inwardly from the walls of the bore. In this position, the post can be moved within the bore, vertically, horizontally or rotationally until the wings are positioned so that mating slots can be formed within the walls of the bore. The mating slots are formed by rotating or oscillating the post with the wings in contact with the wall until the slots in the desired position are formed. The compression force on the legs is released so that the wings are positioned within the mating slots. The noncompressed legs exert little or no expansion force on the bore walls being properly positioned.

BRIEF DESCRIPTION OF THE DRAWINGS

FIGS. 11a–h are cross-sectional views illustrating the installation of a dental post of this invention.

DESCRIPTION OF SPECIFIC EMBODIMENTS

The dental post of this invention includes a means for locking it into the walls of a tooth bore without the requirement of maintaining the post under pressure, selfinduced or otherwise, against the bore walls. The dental post includes a stem having a slot which forms a plurality of legs. At least one leg include a wing extending radially outward from the leg. The wing has a cutting surface which permits formation of a slot into the wall of the bore wall. The wing is shaped to mate with an indentation of the tooth bore wall which is previously formed with the cutting surface of the wing. Each leg can include one or a plurality of wings, each of which mates with a separate indentation in the wall previously formed by the cutting surface of the wings. The legs are sufficiently flexible so that they can be compressed manually or mechanically for ease of insertion into and removal from the tooth bore. When the legs are compressed, so that the wings can fit within the opening of the tooth bore, the post is inserted into the bore. The post is then subjected to a rotational or oscillating force while the wings are in contact with the bore wall to form the indentations of slots. After the slots are formed, the compression force on the legs is released, and the legs resume a position so that they are essentially parallel to each other and the wings fit into the slots or indentation in the bore walls. The wings can be at the same or different heights. The wings can be the same or different sizes. The legs are not prestressed so as to avoid exertion of a force by the legs on the bore walls. By eliminating this stress in the legs, the tooth stub is not subjected to a continuing expansion force from within the tooth stub. Therefore, the tooth stub is less likely to fracture during normal use as compared to a tooth stub containing a dental post that exerts a continuing expansion force. By utilizing the wings as burs, separate burs can be eliminated in order to position the post within the tooth bore.

In cases where the success of the root canal is questionable, the post can be implanted without employing a dental cement in the root canal. The wings mechanically lock the post in place and, together with a key structure described below, lock the post and supported crown in place when the crown is cemented over the post. The elimination of cement within the canal is advantageous since, with present technology, when a root canal fails and a post is present, the post cannot be removed for retreatment of the root canal. This necessitates that surgery be done to the root to eliminate infection. When the post is removable, as in the case when cement within the canal is not utilized, surgery can be avoided and the root canal can be retreated to eliminate infection. However, the post may be cemented and or bonded with micromechanical or chemical etching technique to the dentinal tooth structure utilizing bonding materials and cements such as composites.

In one aspect of this invention, a system, including a template integrally formed within the post, burs and a core for a tooth crown, is provided for use in conjunction with the dental post of this invention. The template is positioned at an intermediate height on the post so as to be positioned on the top surface of the tooth stub when the post is properly positioned in the tooth bore. The template includes holes positioned and shaped to accommodate burs used to form holes on the tooth stub top surface in a shape and design to accommodate a core for a tooth crown or individual separate pins. Separate pins may be placed at an angle relative to the path of insertion and withdrawal of the post to provide retention improvement. Multiple holes will allow trimming of the template for various diameter and shapes of roots. The dental post extends through a central bore of the core. The dental post of this invention also can be provided with wings extending radially from the leg surfaces which wings mate with indentations on the core surface adjacent the dental post. A key apparatus can be provided which fits into the space between the legs in that portion of the dental post which extends above the upper tooth stub surface. The key prevents flexing of the legs after the crown and core have been implanted.

Referring to FIGS. 1 through 4, the dental post 10 formed from any suitable dental material includes a bottom section 12 and a stem section 14. The stem section 14 comprises a plurality of legs 16 formed by virtue of a slot 18 which extends through the thickness of the stem section 14. The use of additional slots results in forming additional legs. For convenience, the dental post 10 is shown with two legs. However, it is to be understood that up to eight legs can be formed conveniently with appropriate slots in stem section 14. The wings 20 and 22 having cutting surfaces as well as wings 50 which do not have cutting surfaces are secured to or formed integrally with the legs 16 such as by conventional molding, machining or casting processes. Wings 50 are optional and the core can be cemented in place. The wings 20 and 22 are preferably positioned at diametrically opposed positions with respect to each other. The cutting surfaces 23, 25 and 27 of each wing are utilized to form the indentations in the tooth bore walls. Cutting surfaces 25 and 27 are optional. In addition, the end surface 23 can end in a point if desired.

The dental post can be made of a variety of sizes. For example, a dental post can extend about 3 to 18 mm into the root and 1 to 7 mm above the root. A typical dental post diameter can vary between about 0.2 mm and 2 mm. The wings can extend a length away from the legs a distance between about 0.1 mm and 1 mm while the slot can vary in width between about 0.1 and 2 mm. It is to be understood that these dimensions are exemplary and will vary with the need of the patient.

Figure 1:
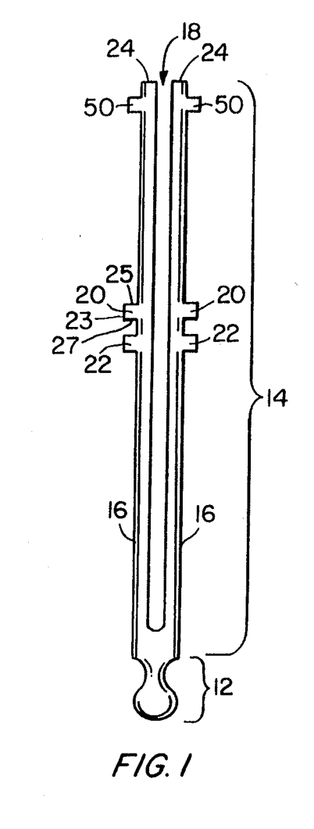
FIG. 1 is a side view of a dental post of this invention.
Figure 1A:
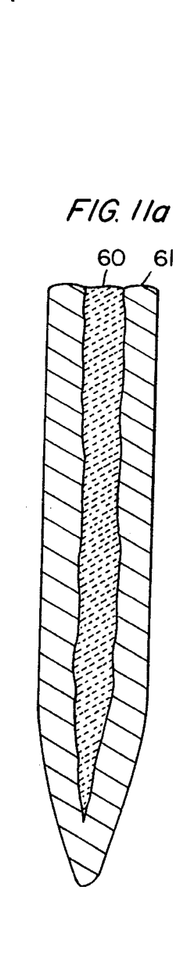
Figure 1B:
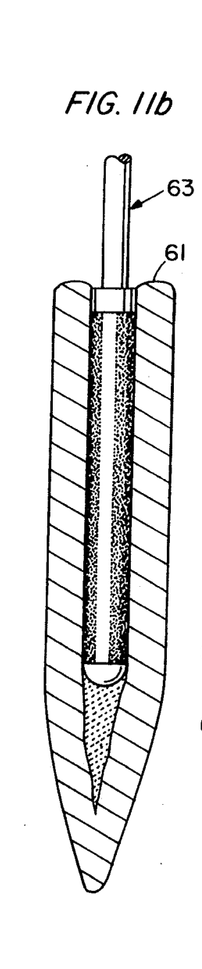
Figures 1C, 1D:
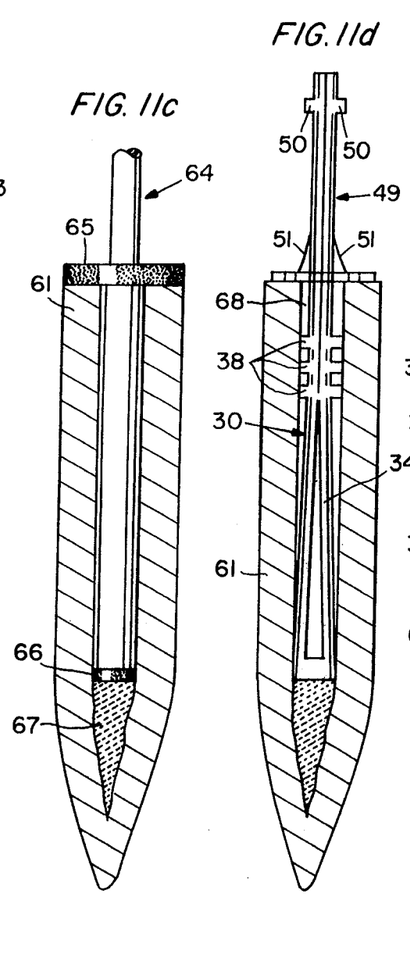
Figure 1E:
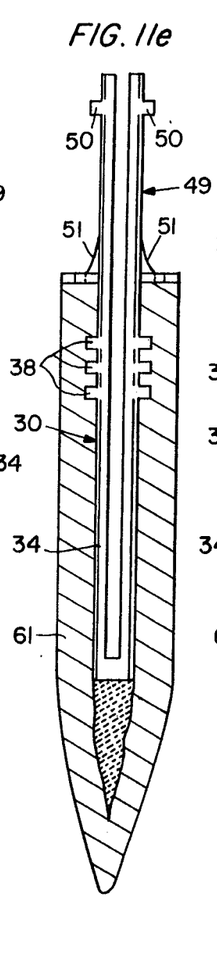
Figure 1F:
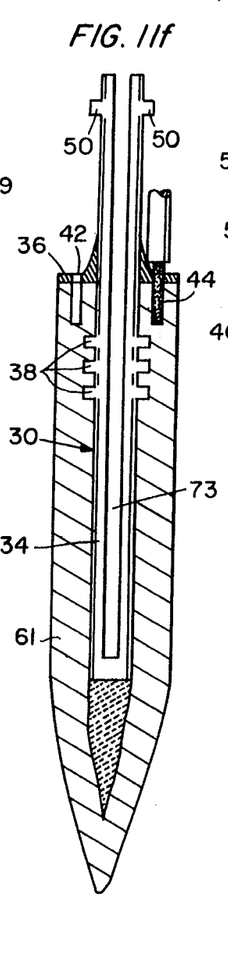
Figure 1G:
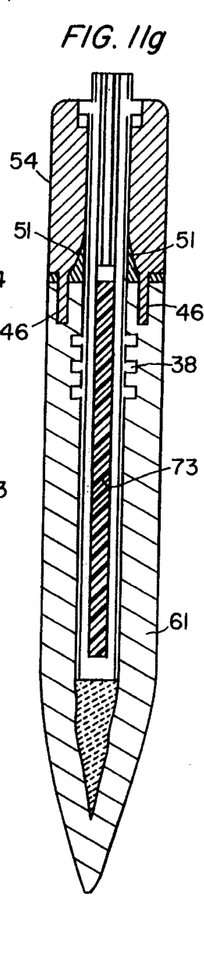
Figure 2:
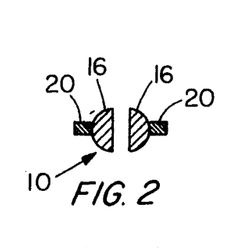
FIGS. 2, 3 and 4 show alternative cross-sections of the legs of the post of FIG. 1 taken along line A—A.
Figure 3:
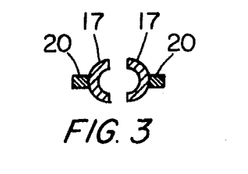
Figure 4:
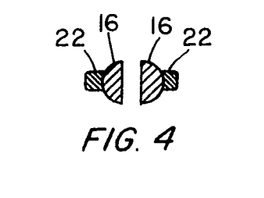

As shown in FIGS. 2 and 4, the legs 16 can have a semi-circular cross-section. As shown in FIG. 3, the legs 17 can have a C-shaped cross-section. The wings 20 can have sharp edges as shown in FIGS. 2 and 3 or the wings 20 or 22 can have a curved edge as shown in FIG. 4. The legs 16 are sufficiently flexible so that they can be compressed manually and the top edges 24 can be contacted with each other. During this compression step, the wings 20 or 22 are moved radically inward toward slot 18.

Figures 5, 6, 7, 8, 9, 10:
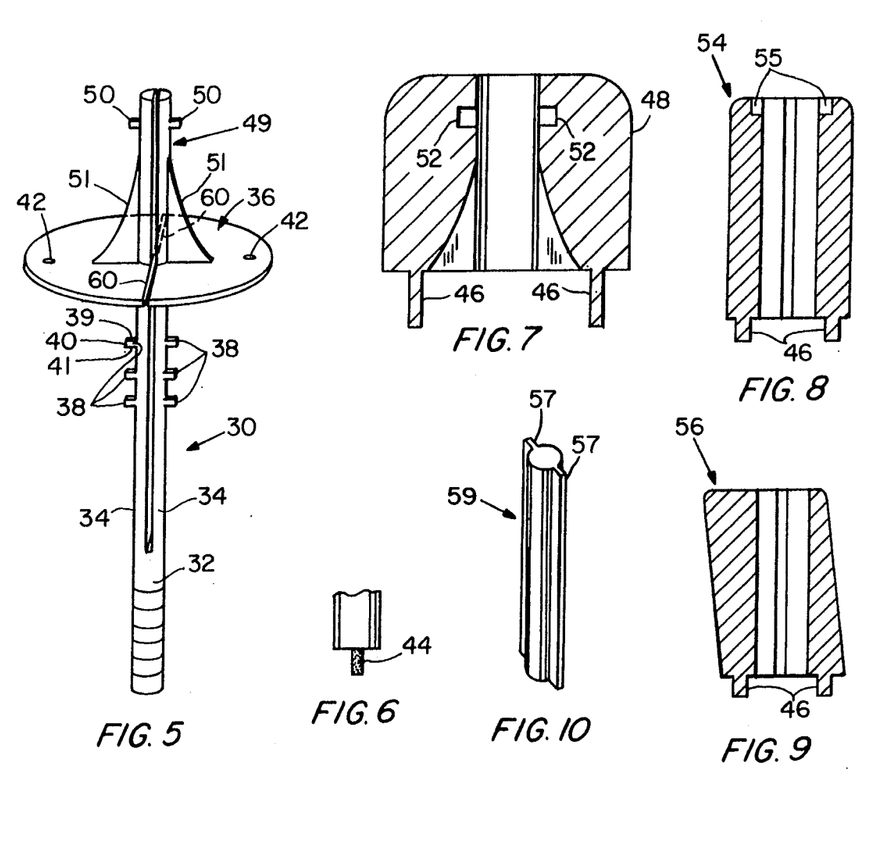
FIG. 5 is a side view of an alternative dental post of this invention.
FIG. 6 is a side view of a bur useful with the post of FIG. 5.
FIG. 7 is a side view of a core which can be utilized in this invention.
FIG. 8 is a cross-sectional view of a core which can be utilized in conjunction with the dental post of this invention.
FIG. 9 is a cross-sectional view of an alternative core which can be utilized in conjunction with the dental post of this invention.
FIG. 10 is an isometric view of a key device which can be utilized in conjunction with the dental post of this invention.

Referring to FIG. 5, an alternative post of this invention is shown. The post 30 includes a stem 32 having two legs 34 and each of which has a plurality of wings 38 having cutting surfaces 39, 40 and 41. Cutting surfaces 39 and 41 are optional. The two legs 34 are compressible so that they can contact each other when compressed. In addition, if desired, the surfaces of legs 34 can comprise cutting surfaces. A template 36 is provided which is positioned at a height so that it contacts the top of a tooth stub when the stem 32 is inserted into the root canal. The template is provided with two holes 42 through which a drill extends (not shown) though more holes may be used. The bur 44 is used to form a hole in the tooth stub for legs 46 of core 48 (FIG. 7). The core 48 includes a central bore to accomodate the top portion 49 of post 30 including wing 50 which do not have cutting surfaces and supporting flanges 51. The flanges 51 provide increased support to the top portion 49 of the post 30. The wings 50 fit into indentations 52 in the core 48. These wings 50 can be eliminated if the core 38 is cemented in place. Alternative cores 54 and 56 are shown respectively in FIGS. 8 and 9 and each having legs 46 which fit into holes 42 of template 36. Core 54 includes indentations 55 for accommodating wings on a dental post. Cores 54 and 56 include vertical slots for accomodating the wings 57 of key 59 (FIG. 10) which wings 59 also can fit into slots 60 in template 36 to prevent rotation of the post 30 and template 36.

Referring to FIGS. 11a–g, the use of the system of this invention is illustrated. As shown in FIG. 11a, an initial tooth bore 60 is formed with a conventional reamer and filled with a conventional filling material such as a gutta percha based material in tooth stub 61. In a second step as shown in FIG. 11b, a bur 63 is used to shape the bore. The final bore shape is formed with bur 64 having a cutting surface 65 and 66 as shown in FIG. 11c. The use of cutting surface 66 is optional. The bottom surface 66 of the bur 64 is flat thereby forming a flat surface on the remaining filling material 67 in the bottom of the bore. The top portion 49 of the post 30 is compressed so that the wings 38 can enter into the bore 68 of tooth stub 61. Compression then is released so that the cutting surfaces of the wings 38 contact the wall of bore 68. The post 30 then is rotated or oscillated while the wings contact the wall so as to form indentations in the walls. The wings then are positioned in the indentations as shown in FIG. 11e. Bur 44 then is inserted into holes 42 of template 36 as shown in FIG. 11f to form holes in tooth stub 61 so that the legs 46 of core 54 can be positioned in the tooth stub 61. As shown in FIG. 11g. An adhesive is placed within the bore 60 to position the post 30 into the bore 60. The post 30 is removed, the adhesive is inseted and the post is reinserted. Excess adhesive passes upwardly within the bore 60 through slot 73 and exits the tooth stub so that a proper amount of adhesive remains within the tooth stub.

Figure 12A:
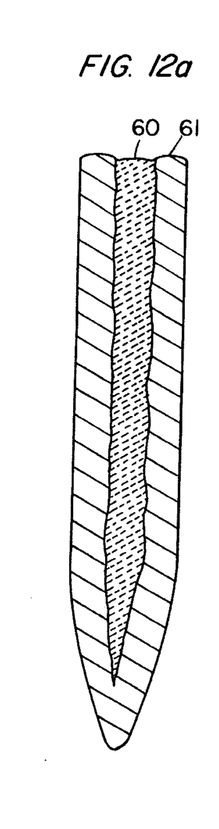
FIGS. 12a–h are cross-sectional views illustrating the installation of an alternative dental post of this invention.
Figure 12B:
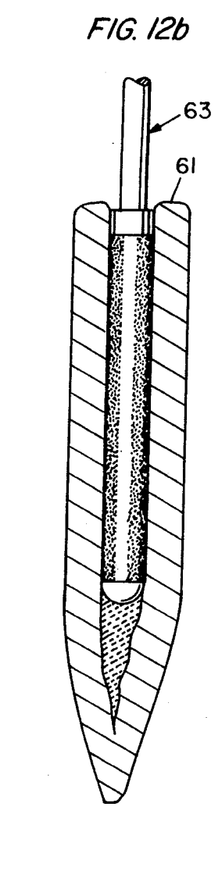
Figure 12C:
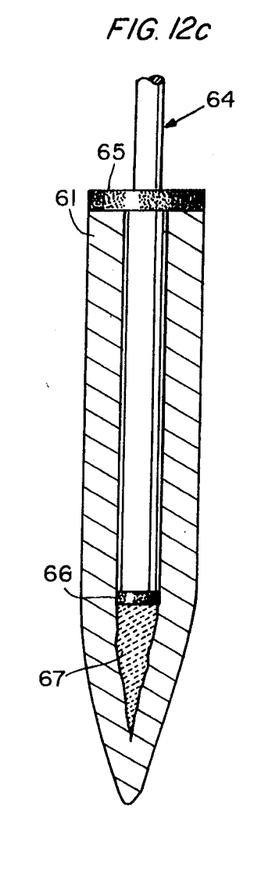
Figure 12D:
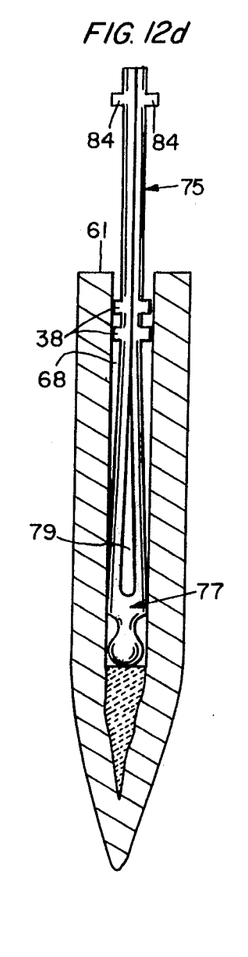
Figure 12E:
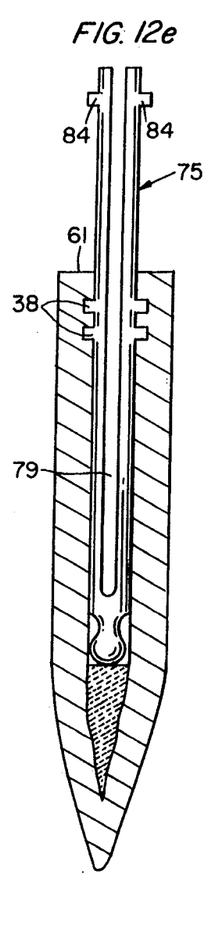
Figure 12F:
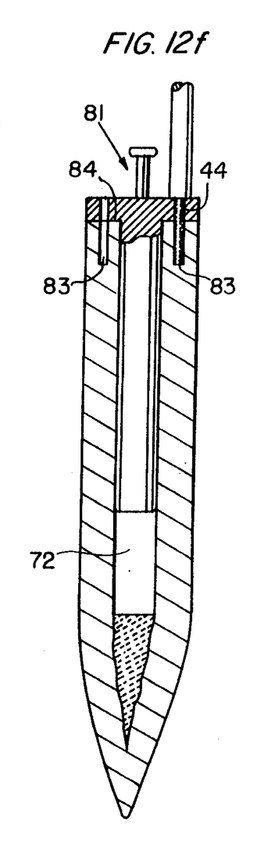
Figure 12G:
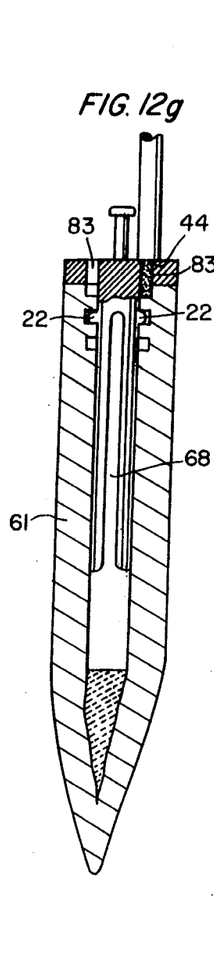
Figure 12H:
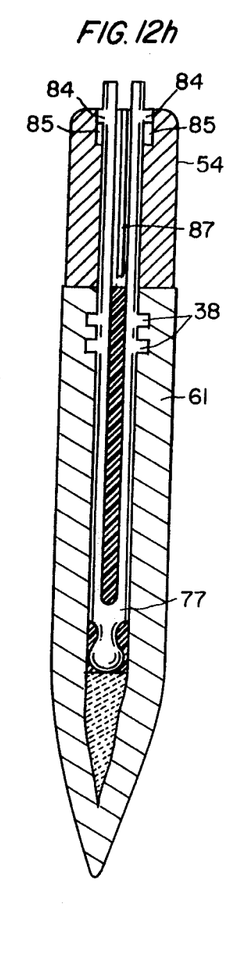
Figure 12I:
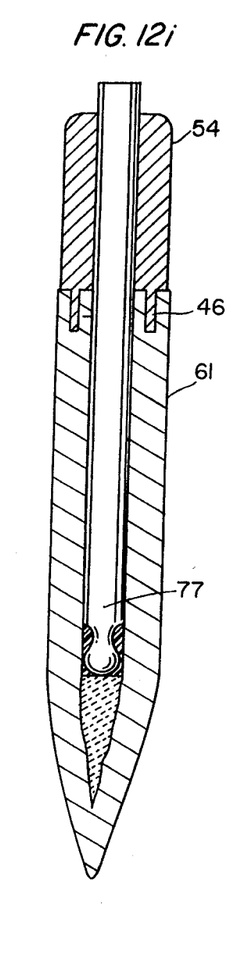

Referring to FIG. 12a to 12i, the use of the system of this invention is illustrated. As shown in FIG. 12a, an initial tooth bore 60 is formed with a conventional reamer and filled with a conventional filling material such as a gutta percha based material in tooth stub 61. In a second step as shown in FIG. 12b, a bur 63 is used to shape the bore. The final bore shape is formed with bur 64 having a cutting surface 65 and 66 as shown in FIG. 11c. The bottom surface 66 of the bur 64 is flat thereby forming a flat surface on the remaining filling material 67 in the bottom of the bore. The cutting disk 65 of the bur 64 has a bottom cutting surface which flattens the tip of tooth stub 61. The top portion 75 of the post 77 is compressed so that the wings 38 can enter into the bore 68 of tooth stub 61. Compression then is released so that the cutting surfaces of the wings 38 contact the wall of bore 68. The post 77 then is rotated or oscillated while the wings contact the wall so as to form indentations in the walls. During rotation or oscillation, a wedge of a flexible material such as rubber can be inserted into space 79 of post 77 to provide a slight expansion force to assist in forming indentations. Template 81 then is inserted into bore 79 and bur 44 is used to form holes 83 through the top surface 84 of tooth stub 61 as shown in FIGS. 12f and 12g. The template 81 can include wings 22 having round surfaces to permit removal of the template by rotating it. Bur 44 then is inserted into holes 83 of template 81 as shown in FIG. 12g to form holes in tooth stub 61 so that the legs 46 of core 54 can be positioned in the tooth stub 61 as shown in 12i. An adhesive is placed within the bore 68 to position the post 77 into the bore 68. Excess adhesive passes upwardly within the bore 60 through slot 79 and exits the tooth stub 61 so that a proper amount of adhesive remains within the tooth stub. As shown in FIGS. 12h and i, the post 77 of this invention is inserted into bore 68 followed by positioning of the core 54 on the tooth surface. The core 54a and b are provided with indentations 85 to mate with wings 84 on the top of post 77. A key 87 is positioned within post 77 so that the wings 84 extend into slots 85 of core 54.

Figure 13:
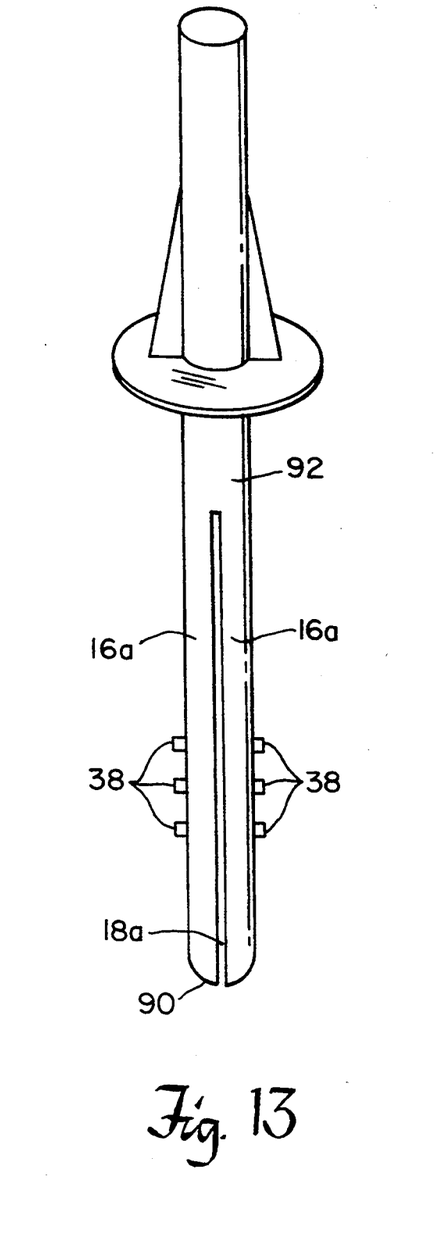
FIG. 13 is an isometric view of an alternative dental post of this invention.

Referring to FIG. 13, an alternative post is shown with a slot 18a which extends from the bottom surface 90 of post 92 to form flexible legs 16a. The wings 38 have outside cutting surfaces and are used as described above.

I claim:

1. A dental post for insertion into a bore of a tooth which comprises:
   a bottom section,
   a stem attached to said bottom section having at least one slot extending lengthwise through said stem to form a plurality of spaced apart legs said legs being substantially parallel to each other and being free of a prestress force,
   at least one of said legs having a wing section extending radially from an outside surface of said legs a distance to fit within an indentation in a wall of said bore in the absence of a force on said legs,
   each of said wing sections having cutting surfaces adapted to form indentations in said wall when said dental post is rotated or oscillated in contact with said wall,
   each of said legs having a length such that a free end of said leg extends beyond a top surface of a tooth when inserted into a bore in said tooth,
   and said legs being movable relative to each other when subjected to a compression force at said free ends such that said wings are removed from an indentation in said wall.

2. The dental post of claim 1 wherein said bottom section includes an indentation extending about its periphery between a bottom surface of said post and a connection between said stem and said bottom section.

3. The dental post of claim 2 wherein at least one of said legs has a plurality of said wings.

4. The dental post of claim 2 wherein at least one wing on each leg is at essentially the same vertical position as a wing on a second leg.

5. The dental post of claim 2 wherein a surface of said legs is roughened.

6. The dental post of claim 1 wherein at least one of said legs has a plurality of said wings.

7. The dental post of claim 1 wherein at least one wing on each leg is at essentially the same vertical position as a wing on a second leg.

8. The dental post of claim 1 wherein a surface of said legs is roughened.

9. The dental post of claim 1 wherein said post includes second wings extending from said legs at a position above a top surface of said tooth, said second wings being free of cutting surfaces.

10. The dental post of any one of claims 1, 2, 6, 3, 7, 4, 8, 5 or 9 having two legs.

11. The dental post of any of claims 1, 2, 6, 3, 7, 4, 8, 5 or 9 and further including a kit further comprising:
   a. a first bur having a cylindrical shaft having a first end surface, a second end surface and an intermediate surface between said first end surface and said second end surface, said intermediate surface comprising a cutting surface,
   and b. a second bur having a cylindrical shaft having an intermediate smooth surface, a first end having a diameter greater than said intermediate smooth surface and having a surface comprising a cutting surface and a second end comprising a cutting surface to form a flat surface on a bottom surface within a bore of a tooth.

12. The dental post of any one of claims 1, 2, 6, 3, 7, 4, 8, 5 or 9 and further including a kit further comprising:
   a. a first bur having a cylindrical shaft having a first end surface, a second end surface and an intermediate surface between said first end surface and said second end surface, said intermediate surface comprising a cutting surface,
   b. a second bur having a cylindrical shaft having an intermediate smooth surface, a first end having a diameter greater than said intermediate smooth surface and having a surface comprising a cutting surface and a second end comprising a cutting surface to form a flat surface on a bottom surface within a bore of a tooth, and c. a template comprising a stem and plate attached to said stem, said stem having a size which permits insertion of said stem within a bore of a tooth, said plate having a first set of holes and a second set of holes, said first set of holes permitting communication of a bur with said bore and a top surface of said tooth and said second set of holes permitting communication of a bur with said top surface of said tooth while preventing communication with said bore.

13. The dental post of claim 12 wherein said plate of said template includes guide means for a bur to form a hole having parallel surfaces in communication with said bore.

14. The dental post of any one of claims 1, 2, 6, 3, 7, 4, 8, 5 or 9 and further comprising a kit further comprising:

a: a first bur having a cylindrical shaft having a first end surface, a second end surface and an intermediate surface between said first end surface and said end surface, said intermediate surface comprising a cutting surface, b. a second bur having a cylindrical shaft having an intermediate smooth surface, a first end having a diameter greater than said intermediate smooth surface and having a surface comprising a cutting surface and a second end comprising a cutting surface to form a flat surface stem having a size which permits insertion of said stem within a bore of a on a bottom surface within a bore of a tooth, c. a template comprising a stem and plate attached to said stem, said tooth, said plate having a first set of holes and a second set of holes, said first set of holes permitting communication of a bur with said bore and a top surface of said tooth and said second set of holes permitting communication of a bur with said top surface of said tooth while preventing communication with said bore, and d. a core of a size to be positioned on a top surface of a tooth, said core having a second bore of a size to permit a portion of said dental post extending above said tooth to be positioned within said second bore, said core having a plurality of legs of a size to be positioned with holes formed by a bur in said second set of holes in said template plate.

15. The dental post of claim 14 wherein said plate of said template includes guide means for a bur to form a hole having parallel surfaces in communication with said bore.

16. The dental post of any one of claims 1, 2, 6, 3, 7, 4, 8, 5 or 9 and further comprising a kit further comprising:

a. a first bur having a cylindrical shaft having a first end surface, a second end surface and an intermediate surface between said first end surface and said end surface, said intermediate surface comprising a cutting surface, b. a second bur having a cylindrical shaft having an intermediate smooth surface, a first end having a diameter greater than said intermediate smooth surface and having a surface comprising a cutting surface and a second end comprising a cutting surface to form a flat surface on a bottom surface within a bore of a tooth, c. a template comprising a stem and plate attached to said stem, said stem having a size which permits insertion of said stem within a bore of a tooth; said plate having a first set of holes and a second set of holes, said first set of holes permitting communication of a bur with said bore and a top surface of said tooth and said second set of holes permitting communication of a bur with said top surface of said tooth while preventing communication with said bore, d. a core of a size to be positioned on a top surface of a tooth, said core having a second bore of a size to permit a portion of said dental post extending above said tooth to be positioned within said second bore, said core having a plurality of legs of a size to be positioned with holes formed by a bur in said second set of holes in said template plate, and e. a key structure of a size and shape to fit within said slot of said post in a portion of said post extending above said tooth.

17. The dental post of claim 16 wherein said plate of said template includes guide means for a bur to form a hole Chalifoux having parallel surfaces in communication with said bore.

18. The dental post of claim 16 wherein said core includes second slots within said second bore and a portion of said key fits within said second slots.

19. The dental post of any one of claims 1, 2, 6, 3, 7, 6, 7, 8 or 9 further comprising a template attached to said legs between said free end of said legs and said wing sections having cutting surfaces.

20. The dental post of any one of claims 1, 2, 6, 3, 7, 4, 8, 5 or 9 further comprising two legs and a template attached to said legs between said free end of said legs and said wing sections having cutting surfaces.

21. A dental post for insertion into a bore of a tooth which comprises:

a top section a stem attached to said top section having at least one slot extending lengthwise through said stem to form a plurality of spaced apart legs, said legs being substantially parallel to each other and being free of a prestressed force, at least one of said legs having a wing section extending radially from an outside surface of said legs a distance to fit within an indentation in a wall of said bore in the absence of a force on said legs, each of said wing sections having cutting surfaces adapted to form indentations in said wall when said dental post is rotated or oscillated in contact with said wall, each of said legs having a length such that said top section extends beyond a top surface of a tooth when inserted into a bore in said tooth, and said legs being movable relative to each other when subjected to a compression force at said free ends such that said wings are removed from an indentation in said wall.

22. The dental post of claim 21 wherein at least one of said legs has a plurality of said wings.

23. The dental post of claim 21 wherein at least one wing on each leg is at essentially the same vertical position as a wing on a second leg.

24. The dental post of claim 21 wherein a surface of said legs is roughened.

25. The dental post of claim 21 wherein said post includes second wings extending from said top section at a position above a top surface of said tooth, said second wings being free of cutting surfaces.

26. The dental post of any one of claims 21, 22, 23, 24 or 25 further comprising a template attached to said top section.

27. The dental post of any one of claims 21, 22, 23, 24 or 25 further comprising two legs and a template attached to said top section.

28. The dental post of any one of claims 21, 22, 23, 24 or 25 and further including a kit further comprising:
   a. a first bur having a cylindrical shaft having a first end surface, a second end surface, and an intermediate surface between said first end surface and said second end surface comprising a cutting surface,
   and b. a second bur having a cylindrical shaft having an intermediate smooth surface, a first end having a diameter greater than said intermediate smooth surface and having a surface comprising a cutting surface and a second end comprising a cutting surface to form a flat surface on a bottom surface within a bore of a tooth.

29. The dental post of any one of claims 21, 22, 23, 24 or 25 and further including a kit further comprising:
   a. a first bur having a cylindrical shaft having a first end surface, a second end surface and an intermediate surface between said first end surface and said second end surface, said intermediate surface comprising a cutting surface,
   b. a second bur having a cylindrical shaft having an intermediate smooth surface, a first end having a diameter greater than said intermediate smooth surface and having a surface comprising a cutting surface and a second end comprising a cutting surface to form a flat surface on a bottom surface within a bore of a tooth,
   and c. a template comprising a stem and plate attached to said stem, said stem having a size which permits insertion of said stem within a bore of a tooth, said plate having a first set of holes and a second set of holes, said first set of holes permitting communication of a bur with said bore and a top surface of said tooth and said second set of holes permitting communication of a bur with said top surface of said tooth while preventing communication with said bore.

30. The dental post of claim 29 wherein said plate of said template includes guide means for a bur to form a hole having parallel surfaces in communication with said bore.

31. The dental post of any one of claims 21, 22, 23, 24 or 25 and further including a kit further comprising:
   a. a first bur having a cylindrical shaft having a first end surface, a second end surface and an intermediate surface between said first end surface and said end surface, said intermediate surface comprising a cutting surface,
   b. a second bur having a cylindrical shaft having an intermediate smooth surface, a first end having a diameter greater than said intermediate smooth surface and having a surface comprising a cutting surface and a second end comprising a cutting surface to form a flat surface on a bottom surface within a bore of a tooth,
   c. a template comprising a stem and plate attached to said stem, said stem having a size which permits insertion of said stem within a bore of a tooth, said plate having a first set of holes and a second set of holes, said first set of holes permitting communication of a bur with said bore and a top surface of said tooth and said second set of holes permitting communication of a bur with said top surface of said tooth while preventing communication with said bore,
   and d. a core of a size to be positioned on a top surface of a tooth, said core having a second bore of a size to permit a portion of said dental post extending above said tooth to be positioned within said second bore, said core having a plurality of legs of a size to be positioned within holes formed by a bur in said second set of holes in said template plate.

32. The dental post of claim 31 wherein said plate of said template includes guide means for a bur to form a hole having parallel surfaces in communication with said bore.

33. The dental post of any one of claims 21, 22, 23, 24 or 25 and further including a kit further comprising:
   a. a first bur having a cylindrical shaft having a first end surface, a second end surface and an intermediate surface between said first end surface and said end surface, said intermediate surface comprising a cutting surface,
   b. a second bur having a cylindrical shaft having an intermediate smooth surface, a first end having a diameter greater than said intermediate smooth surface and having a surface comprising a cutting surface and a second end comprising a cutting surface to form a flat surface on a bottom surface within a bore of a tooth,
   c. a template comprising a stem and plate attached to said stem, said stem having a size which permits insertion of said stem within a bore of a tooth, said plate having a first set of holes and a second set of holes, said first set of holes permitting communication of a bur with said bore and a top surface of said tooth and said second set of holes permitting communication of a bur with said top surface of said tooth while preventing communication with said bore,
   d. a core of a size to be positioned on a top surface of a tooth, said core having a second bore of a size to permit a portion of said dental post extending above said tooth to be positioned within said second bore, said core having a plurality of legs of a size to be positioned with holes formed by a bur in said second set of holes in said template plate,
   e. a key structure of a size and shape to fit within said slot of said post in a portion of said post extending above said tooth.

34. The dental post of claim 33 wherein said plate of said template includes guide means for a bur to form a hole having parallel surfaces in communication with said bore.

35. The dental post of claim 33 wherein said core includes second slots within said second bore and a portion of said key fits within said second slots.

* * * * *